United States Patent [19]

Kukes

[11] 4,368,141
[45] Jan. 11, 1983

[54] OLEFIN DISPROPORTIONATION AND CATALYST THEREFOR

[75] Inventor: Semyon Kukes, Bartlesville, Okla.

[73] Assignee: Phillips Petroleum Company, Bartlesville, Okla.

[21] Appl. No.: 276,777

[22] Filed: Jun. 24, 1981

[51] Int. Cl.$^3$ .......................... B01J 27/02; C07C 5/25
[52] U.S. Cl. .................................. 252/439; 585/371; 585/601; 585/646
[58] Field of Search ................ 252/439; 585/371, 601, 585/646

[56] References Cited

U.S. PATENT DOCUMENTS

| | | | |
|---|---|---|---|
| 3,340,322 | 9/1967 | Heckelsberg | 260/683 |
| 3,418,390 | 12/1968 | Heckelsberg | 260/683 |
| 3,519,556 | 7/1970 | Seautt | 208/111 |
| 3,952,070 | 4/1976 | Nowak et al. | 585/646 |

OTHER PUBLICATIONS

R. L. Banks, "Catalytic Olefin Disproportionation", *Fortschitte der Chemischen Forschung*, vol. 25, pp. 41, 67.

*Primary Examiner*—Thomas A. Waltz

[57] ABSTRACT

A novel disproportionation catalyst comprising the product resulting from the combination of elemental sulfur and a disproportionation catalyst consisting essentially of a refractory oxide containing molybdenum oxide or tungsten oxide.

16 Claims, No Drawings

OLEFIN DISPROPORTIONATION AND CATALYST THEREFOR

BACKGROUND OF INVENTION

This invention relates to the disproportionation of olefins. In another aspect this invention relates to a disproportionation catalyst. In still another aspect, this invention relates to a novel method for producing a disproportionation reaction.

The disproportionation, or metathesis, of olefins is a reaction in which one or more olefinic compounds are transformed into other olefins of different molecular weights. The disproportionation of an olefin to produce one olefin of a higher molecular weight and one olefin of a lower molecular weight can also be referred to as self-disproportionation. For example, propene can be disproportionated to ethylene and cis- and trans-2-butene. Another type of disproportionation involves the codisproportionation of two different olefins to form still other olefins. An example would be the reaction of one molecule of 2-butene with one molecule of 3-hexene to produce two molecules of 2-pentene.

The term "disproportionation reaction" as used herein is intended to include all variations of disproportionation reactions including:

(1) The disproportionation of an acyclic mono- or polyene having at least three carbon atoms into other mono- or polyenes of both higher and lower number of carbon atoms; for example, the disproportionation of propylene yields ethylene and butenes; the disproportionation of 1,5-hexadiene yields ethylene and 1,5,9-decatriene;

(2) The conversion of an acyclic mono- or polyene having three or more carbon atoms and a different acyclic mono- or polyene having three or more carbon atoms to produce different acyclic olefins; for example, the conversion of propylene and isobutylene yields ethylene and isopentene;

(3) The conversion of ethylene and an internal acyclic mono- or polyene having four or more carbon atoms to produce other olefins having a lower number of carbon atoms than that of the acyclic mono- or polyenes; for example, the conversion of ethylene plus 4-methylpentene-2 yields 3-methylbutene-1 and propylene;

(4) The conversion of ethylene or an acyclic mono- or polyene having three or more carbon atoms with a cyclic mono- or cyclic polyene to produce an acyclic polyene having a higher number of carbon atoms than that of any of the starting materials; for example, the conversion of cyclohexene and 2-butene yields 2,8-decadiene; the conversion of 1,5-cyclooctadiene and ethylene yields 1,5,9-decatriene;

(5) The conversion of one or more cyclic mono- or cyclic polyenes to produce a cyclic polyene having a higher number of carbon atoms than any of the starting materials; for example, the conversion of cyclopentene yields 1,6-cyclodecadiene;

(6) The conversion of an acyclic polyene having at least 7 carbon atoms and having at least 5 carbon atoms between any two double bonds to produce acyclic and cyclic mono- and polyenes having a lower number of carbon atoms than that of the feed; for example, the conversion of 1,7-octadiene yields cyclohexene and ethylene; or (7) The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-pentadiene yields 1,4-cyclohexadiene and ethylene.

Among the catalysts that have been developed for disproportionation are those comprising inorganic refractory oxides containing a catalytic amount of at least one of molybdenum oxide and tungsten oxide. The present invention is based upon the discovery of a way to improve the characteristics of such a catalyst.

SUMMARY OF INVENTION

In accordance with the present invention, a disproportionation catalyst comprising inorganic refractory oxide containing a catalytic amount of at least one of molybdenum oxide and tungsten oxide is improved by admixing therewith a promoting amount of elemental sulfur and then activating the admixture at an elevated temperature under an inert atmosphere.

DESCRIPTION OF PREFERRED EMBODIMENTS

The inorganic refractory oxide comprises solid inorganic oxide support containing a major proportion of alumina or silica. Such materials are commonly known as refractory oxides and include, for example, silica, alumina, magnesia-alumina, silica-alumina, titania-alumina, zirconia-alumina, and alumina-titania-zirconia. Preferred refractory metal oxides are alumina refractory oxides, i.e., refractory oxides containing a substantial proportion of alumina, e.g., at least 10 percent by weight of alumina, preferably at least 25 percent of alumina, although still larger proportions of alumina can be used. Generally, the refractory oxide has a surface area of at least 10 $m^2/g$ and preferably the surface area is from about 25 $m^2/g$ to 800 $m^2/g$.

Molybdenum oxide and tungsten oxide can be combined with the refractory oxide support in any conventional manner such as dry mixing, impregnation from a diluent, ion-exchange or the like. The oxides can be added directly or in the form of molybdenum or tungsten that can be converted to oxides by calcination.

The molybdenum or tungsten oxide-alumina composition employed as a catalyst precursor is optionally, and preferably, subjected to pretreatment prior to utilization in preparation of the catalyst. The precise method of pretreatment will depend in part upon the form of chemical combination in which the molybdenum or tungsten components are provided, but in general the pretreatment comprises heating an initially prepared molybdenum or tungsten containing alumina refractory oxide in an atmosphere of a non-reducing gas such as nitrogen, argon, carbon monoxide or oxygen-containing gas, e.g., air. One function served by this type of pretreatment is to convert the molybdenum or tungsten components into the form of the oxide if these components are not initially provided in these forces. For example, initial catalyst components such as ammonium tungstate or ammonium molybdate are converted to the corresponding oxide by heating in a non-reducing atmosphere. The pretreatment temperature is not critical and temperatures from about 350° C. to 800° C. are satisfactory.

The oxide of molybdenum or tungsten is preferably combined with the inorganic oxide solid support in a high positive oxidation state, e.g., hexavalent molybdenum or hexavalent tungsten. The proportion of the molybdenum or tungsten oxide combined with the alumina-containing inorganic oxide can be varied, but generally the inorganic oxide solid contains at least 0.1 percent by weight of the oxide of molybdenum or tungsten with amounts from about 0.2 percent to about 50 percent by weight being preferred, although still larger (major) proportions of molybdenum or tungsten oxide can be used.

The elemental sulfur can be combined with the thus prepared catalyst in any suitable manner. One technique involves physically admixing the catalyst and the sulfur. Another technique involves merely placing the elemental sulfur on the surface of a bed of the catalyst and then flowing heated inert gas through the sulfur and into the catalyst bed.

The heating under an inert atmosphere can be conducted at any temperature which results in an improved catalyst. Generally, this involves heating at a temperature in the range of 500° C. to about 800° C., more preferably in the range of about 550° C. to 650° C. The optimum time for the heating step can be determined by routine experimentation. Typically heating times in the range of 30 minutes to 1.5 hours have been found particularly suitable.

The amount of sulfur employed can vary over a wide range. Generally, the sulfur is employed in an amount of about 0.01 to about 5 weight percent, preferably less than 3 weight percent, based on the weight of the metal oxide support combination prior to the addition of the dithionite.

The starting catalysts can be prepared by any of the techniques known in the art. For example, a 6 weight percent $WO_3.SiO_2$ can be prepared by dissolving 2.31 g of ammonium metatungstate in 75 milliliters of water and then combining that solution with 33 grams of $SiO_2$ suspended in 100 milliliters of water. After sitting for about an hour, the catalyst is then dried to produce a material suitable for calcination.

The promoted catalyst can be used in disproportionation reactions in a conventional manner. Typically, the disproportionation is carried out at a temperature in the range of about 20° to about 600° C.

The disproportionation reaction can be carried out by contact the olefins to be disproportionated with the catalyst in the liquid phase or the gas phase, depending on structure and molecular weight of the olefins, temperature and pressure.

The pressure during the disproportionation reaction may vary between wide limits. Pressures between 0.1 and 500 atm. are suitable; preferred pressures are between 0.5 and 250 atm. If possible, the process should be operated at a pressure which is atmospheric or nearly atmospheric so that no vacuum or pressure apparatus is required.

If the reaction is carried out in the liquid phase, solvents or diluents for the reactants may be used. Aliphatic saturated hydrocarbons (e.g. pentane, hexane, cyclohexane, dodecane) and aromatic hydrocarbons such as benzene and toluene are suitable. If the reaction is carried out in the gaseous phase, diluents such as aliphatic hydrocarbons (e.g. methane, ethane) and/or inert gases (e.g., nitrogen, carbon dioxide) may be present. Preferably the disproportionation reaction is effected in the substantial absence of reactive materials such as water and oxygen.

The length of time during which the olefinically unsaturated compounds to be disproportionated are contacted with the catalyst is not very critical, and may conveniently vary between 5 seconds and 24 hours, although longer and shorter contact times may be used. The contact time needed to obtain a reasonable yield of disproportionated products depends on several factors such as the activity of the catalyst, temperature, pressure and structure of the olefinically unsaturated compounds to be disproportionated.

The process of the invention is effected batchwise or continuously, with fixed catalyst beds, slurried catalysts, fluidized beds or by using any other conventional contacting technique. The solid disproportionation catalysts are applied in any appropriate form, for example, as powders, flakes, pellets, spheres or extrudates.

The Products.

According to the process of the invention two olefinic reactants are disproportionated to a product comprising olefin(s) having a total number of carbon atoms equal to the sum of the carbon atoms of the two olefinic reactants and having a number of ethylenic linkages equal to the sum of the ethylenic double bonds of the reactants.

One variation of the process comprises the disproportionation of two molecules of the same olefinic reactant. The reaction of two molecules of an acyclic olefin of Formula I generally produces one olefin of a higher carbon number and one olefin of a lower carbon number as depicted in equation (1)

$$2 \text{ RCH}=\text{CHR}' \longrightarrow \text{RCH}=\text{CHR} + \text{R'CH}=\text{CHR}' \quad (1)$$

I wherein R and R' have the previously stated significance. If R and R' represent identical groups, it is appreciated that the disproportionation reaction will not cause any skeletal changes as the products RCH=CHR and R'CH=CHR' will be equivalent to R'CH=CHR. By way of specific illustration, the reaction of two molecules of propylene produces ethylene and 2-butene. However, the reaction of two molecules of 2-butene produces two molecules of 2-butene. The reaction of two molecules of cyclic olefinic reactant of Formula II, however, produces a single cyclic olefin produced as depicted in equation (2)

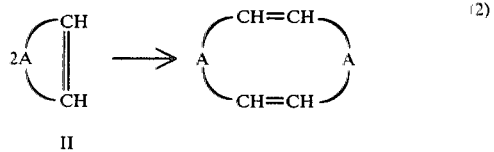

II

By way of specific illustration, the reaction of two molecules of cyclooctene produces 1,9-cyclohexadecadiene.

Another variation of the process comprises the disproportionation of two different acyclic olefinic reactants. By way of specific illustration, the reaction of 2-butene and 3-hexene produces two molecules of 2-pentene and the reaction of 2-butene with 1,4-polybutadiene produces two molecules of 1,4-polybutadiene having a molecular weight which is less than the molecular weight of the starting 1,4-polybutadiene.

Still another variation of the process is "ring-opening" disproportionation wherein an acyclic olefinic reactant represented by Formula I is contacted with a cyclic olefinic reactant represented by Formula II. The product of "ring-opening" is a single olefinic compound with one less carbocyclic ring than the cyclic olefinic reactant of Formula II. In terms of the Formulas I and II, the product is represented by Formula III.

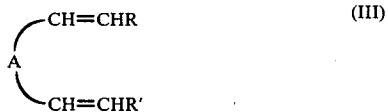

wherein R, R' and A have previously stated significance. By way of specific illustration, from reaction of 2-butene and cyclopentene is produced 2,7-nonadiene. Other typical products include 2,8-decadiene produced by reaction of cyclohexene and 2-butene, 3,8-undecadiene produced from 3-hexene and cyclopentene, 1,5,9-decatriene produced by reaction of ethylene and 1,5-cyclooctadiene, and 1,4-divinylcyclohexane from ethylene and bicyclo(2.2.2)oct-2-ene.

In "ring-opening" disproportionation, the cyclic olefinic reactant is preferably a monocyclic or a bicyclic olefinic reactant of up to two ethylenic linkages and most preferably is a monocyclic, mono-olefinic reactant of from five to eight carbon atoms, and the acyclic olefinic reactant is preferably an internal olefin which is symmetrical about the double bond, i.e., those olefins wherein both R and R' groups are alkyl and R=R'. The molar ratio of cyclic olefinic reactant to the acyclic olefin in ring-opening disproportionation is not critical, although it is frequently useful to employ a molar excess of the acyclic olefin. Molar ratios of acyclic olefin to cyclic olefin reactant from about 1:1 to about 70:1 are satisfactory with molar ratios from about 1:1 to about 10:1 being preferred.

It is appreciated that an olefinic product produced by any variation of the disproportionation process can undergo further disproportionation with another olefin present in the reaction mixture. For example, 1,6-heptadiene produced from reaction of cyclopentene and ethylene can react with another molecule of cyclopentene to produce 1,6,11-dodecatriene, and 1,9-cyclohexadecadiene produced from reaction of two molecules of cyclooctene to give a high molecular weight monocyclic polyene.

The olefinic products, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are treated with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated by conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by the following examples:

EXAMPLE I

One gram of a $MoO_3.SiO_2$ composition containing 8 weight percent $MoO_3$ was placed in a tubular quartz reactor of the type generally used for disproportionation reactions. About 0.03 gram of elemental sulfur was placed on top of the catalyst and then the mixture was heated at 600° C. while nitrogen was flowed through the catalyst for 30 minutes.

The resulting composition was then tested for catalytic activity using purified propylene as reactant. The disproportionation reaction was conducted at 353° C. with a propylene feed rate of 107 cc/minute.

For comparison the propylene was disproportionated under substantially the same reaction conditions using the same $MoO_3.SiO_2$ composition but without any sulfur treatment. The reaction temperatures for the control was slightly higher, i.e., about 356° C. The results are summarized in the following table:

TABLE I

| | Propylene Conversion | | | | | |
|---|---|---|---|---|---|---|
| | 5 min. | 15 min. | 30 min. | 60 min. | 75 min. | 90 min. |
| Control $MoO_3.SiO$ | 2 | 7 | 10 | 12 | 11 | 11 |
| Sulfur Treated $MoO_3.SiO$ | 8 | 20 | 21 | 21 | 20 | — |

The results indicate that the sulfur treatment resulted in a remarkable improvement in the activity of the $MoO_3$ catalyst.

EXAMPLE II

One gram of a $WO_3.SiO_2$ composition containing 6 weight percent $WO_3$ was placed in a tubular quartz reactor as in Example I. About 0.03 gram of elemental sulfur was placed on top of the catalyst and then the mixture was heated at 620° C. while nitrogen was flowed through the catalyst for 30 minutes. A grey-blue composition resulted. Elemental analysis indicated that the composition contained about 0.05 weight percent sulfur.

The resulting composition was then tested for catalytic activity using purified propylene as reactant. The disproportionation reaction was carried out at 455° C. with a propylene feed rate of about 104 cc/minute.

For comparison, the propylene was also reacted under the same conditions using the same $WO_3.SiO_2$ composition but without the sulfur treatment. The results are summarized in the following table:

TABLE II

| | Propylene Conversion | | | | | |
|---|---|---|---|---|---|---|
| | 5 min. | 15 min. | 30 min. | 60 min. | 75 min. | 90 min. |
| Control $WO_3.SiO_2$ | 2 | 4 | 8 | 13 | 14 | 15 |
| Sulfur Treated $WO_3.SiO_2$ | 20 | 25 | 25 | 26 | 26 | 27 |

These results indicate that the sulfur treatment also provided a remarkable improvement in the activity of the $WO_3.SiO_2$ catalyst.

EXAMPLE III

This example is provided to compare the instant catalyst system to the prior art sulfur containing catalyst.

A $WO_3.SiO_2$ composition containing 6 weight percent $WO_3$ was sulfided with $H_2S$, 5 hours at 460° F. and then 5 hours at 700° F. A black catalyst resulted which is denoted herein as $WS_2.SiO_2$. About 1.5 grams of the $WS_2.SiO_2$ was placed in a tubular reactor under nitrogen and heated at 620° C. for 1.5 hours. The temperature was then decreased to 500° C. and dried propylene was flowed therethrough at a rate of 150 cc/minute.

After about 90 min. of disproportionation, the propylene feed was discontinued and the catalyst calcined at 620° C. while flowing 100 cc/minute of air for 1 hour. Then the catalyst was flushed with nitrogen and propylene disproportionation again carried out as before. The calcined catalyst is considered to be substantially $WO_3.SiO_2$.

After about 120 minutes of disproportionation, the catalyst was calcined for 1 hour at 550° C. To the calcined catalyst was added 0.01 gram of elemental sulfur and then nitrogen flow for 1 hour at 620° C. was used to distribute the sulfur through the catalyst. The resulting catalyst was then used for the disproportionation of propylene under the same conditions as before.

The relative effects of the three catalysts are illustrated in the following table:

TABLE III

|  | Propylene Conversion | | | | | | |
| --- | --- | --- | --- | --- | --- | --- | --- |
|  | 3 min. | 15 min. | 30 min. | 45 min. | 60 min. | 75 min. | 90 min. |
| $WS_2.SiO_2$ | 2 | 2.5 | 3.1 | 5.4 | 6.5 | 7.4 | 8.6 |
| $WO_3.SiO_2$ Sulfur Treated | 3.1 | 10.2 | 16.3 | 20.8 | 23.1 | 26.4 | 27.9 |
| $WO_3.SiO_2$ | 14.8 | 27.2 | 33.7 | 37.2 | 38.2 | 39.5 | 40.4 |

These results indicate that the $WO_3.SiO_2$ catalyst is more active than the $WS_2.SiO_2$ catalyst and that the inventive sulfur treatment results in a catalyst that is even more active then the $WO_3.SiO_2$ catalyst.

What is claimed is:

1. A method of preparing a disproportionation catalyst comprising admixing elemental sulfur with a catalyst consisting essentially of a refractory oxide containing a metal oxide selected from the group consisting of molybdenum oxide and tungsten oxide and activating the catalyst by heating in the presence of an inert gas.

2. A method according to claim 1 wherein said inorganic refractory oxide is selected from the group of silica, alumina, and mixtures thereof.

3. A method according to claim 2 wherein said metal oxide is in the range of about 1 to about 10 percent of the combined weight of said metal oxide and said refractory oxide prior to the addition of the elemental sulfur.

4. A method according to claim 3 wherein the elemental sulfur is employed in an amount in the range of about 0.01 to about 5 weight percent based on the weight of the metal oxide-refractory oxide combination prior to the addition of the elemental sulfur.

5. A method according to claim 4 wherein said metal oxide is $WO_3$ and said refractory oxide is $SiO_2$.

6. A method according to claim 5 wherein said elemental sulfur is employed in an amount in the range of about 0.01 to about 1 weight percent based on the weight of the metal oxide-refractory oxide combination prior to the addition of the elemental sulfur.

7. A method according to claim 6 wherein said catalyst is activated by heating at a temperature in the range of 550° C. to 650° C.

8. A method according to claim 7 wherein said elemental sulfur is placed on top of a bed of the starting catalyst and said sulfur is admixed with the catalyst as a result of an inert gas which flows through the sulfur and then through the catalyst.

9. A method according to claim 4 wherein said metal oxide is $MoO_3$ and said refractory oxide is $SiO_2$.

10. A method according to claim 9 wherein said elemental sulfur is employed in an amount in the range of about 0.01 to about 1 weight percent based on the weight of the metal oxide-refractory oxide combination prior to the addition of the elemental sulfur.

11. A method according to claim 10 wherein said catalyst is activated by heating at a temperature in the range of 550° C. to 650° C.

12. A method according to claim 11 wherein said elemental sulfur is placed on top of a bed of the starting catalyst and said sulfur is admixed with the catalyst as a result of an inert gas which flows through the sulfur and then through the catalyst.

13. A composition prepared in accordance with any one of claims 1-12.

14. A process for the disproportionation of olefins comprising contacting said olefins under suitable reaction conditions with a catalytic amount of a catalyst composition prepared in accordance with a method of claims 1-12.

15. A process according to claim 14 wherein said disproportionation is carried out at a temperature in the range of about 20° C. to about 600° C.

16. A process according to claim 15 wherein said olefin reactant comprises propylene.

* * * * *